US012737407B2

(12) United States Patent
Hou

(10) Patent No.: US 12,737,407 B2
(45) Date of Patent: Sep. 15, 2026

(54) SYSTEM FOR HELPING OPERATOR TO QUESTION HELP-SEEKER

(71) Applicant: NCNCD, China CDC, Beijing (CN)

(72) Inventor: Lei Hou, Beijing (CN)

(73) Assignee: NATIONAL CENTER FOR CHRONIC AND NONCOMMUNICABLE DISEASE CONTROL AND PREVENTION, CHINESE CENTER FOR DISEASE CONTROL AND PREVENTION, Beijing (CN)

( * ) Notice: Subject to any disclaimer, the term of this patent is extended or adjusted under 35 U.S.C. 154(b) by 0 days.

(21) Appl. No.: 18/866,763

(22) PCT Filed: Jul. 4, 2023

(86) PCT No.: PCT/CN2023/105651
§ 371 (c)(1),
(2) Date: Nov. 18, 2024

(87) PCT Pub. No.: WO2024/008056
PCT Pub. Date: Jan. 11, 2024

(65) Prior Publication Data

US 2026/0057001 A1 Feb. 26, 2026

(30) Foreign Application Priority Data

Jul. 8, 2022 (CN) ......................... 202210805597.1

(51) Int. Cl.
*G06F 16/35* (2025.01)
*G06F 40/30* (2020.01)
*G16H 80/00* (2018.01)

(52) U.S. Cl.
CPC ............. *G06F 16/35* (2019.01); *G06F 40/30* (2020.01); *G16H 80/00* (2018.01)

(58) Field of Classification Search
CPC .......... G06F 16/35; G06F 40/30; G16H 80/00
(Continued)

(56) References Cited

U.S. PATENT DOCUMENTS 10,977,452 B2 * 4/2021 Wang .................. G10L 15/1822
11,763,949 B1 * 9/2023 Shields .................. G16H 50/20
705/2
(Continued)

FOREIGN PATENT DOCUMENTS

CN 113360622 A 9/2021
CN 114637841 A 6/2022
(Continued)

OTHER PUBLICATIONS

Demner-Fishman, Dina, et al., "Answer Extraction, Semantic Clustering, and Extractive Summarization for Clinical Question Answering", Proc. of the 21st International Conf. on Computational Linguistics and 44th Annual Meeting of the ACL, Sydney, Australia, Jul. 2006, pp. 841-848.*
(Continued)

*Primary Examiner* — Robert Stevens
(74) *Attorney, Agent, or Firm* — Thomas Horstemeyer, LLP

(57) ABSTRACT

A system for helping an operator to question a help-seeker is provided. The system includes: taking the positive probability of any second reference group included as a cut-off point, and performing a classification test on any first reference group to obtain a classification sensitivity and a classification specificity corresponding to any second reference group; based on the classification sensitivities and the classification specificities corresponding to a plurality of second reference groups amongst any first reference group, obtaining a receiver operating characteristic curve corresponding to any first reference group; according to the
(Continued)

receiver operating characteristic curve, determining a target first reference group from the plurality of first reference groups; and according to the distance between a coordinate point corresponding to any second reference group amongst the plurality of second reference groups and a perfect classification coordinate point, determining a target question semantic meaning.

12 Claims, 8 Drawing Sheets

(58) Field of Classification Search
USPC .......................................................... 707/737
See application file for complete search history.

(56) References Cited

U.S. PATENT DOCUMENTS 11,782,981 B2 * 10/2023 Xu ........................ G06F 16/288 707/794
2011/0218253 A1 * 9/2011 Lange .................... G16H 50/70 514/789
2011/0301982 A1 * 12/2011 Green, Jr. .............. G16H 40/67 705/3
2012/0191716 A1 * 7/2012 Omoigui ............. H10F 39/1825 707/E17.069
2014/0249850 A1 * 9/2014 Woodson ............... G16H 10/60 705/3
2016/0328530 A1 * 11/2016 Felemban ............ A61B 5/0024
2019/0163875 A1 * 5/2019 Allen ..................... G16H 50/70

FOREIGN PATENT DOCUMENTS

CN 115346690 A 11/2022
WO 2021196981 A1 10/2021

OTHER PUBLICATIONS

Olson, Catherine H., et al., "Clustering of elderly patient subgroups to identify medication-related readmission risks", International Journal of Medical Informatics, vol. 85, Issue 1, Jan. 2016, pp. 43-52.*
Aftab, Rana Mohtasham, "A systematic review of data-driven & machine learning frameworks for minimizing emergency response rate", International Journal of Natural Sciences Research, vol. 11, No. 2, Oct. 9, 2023, pp. 52-64.*
Chan, Hao-Yung, et al., "Question-answering dialogue system for emergency operations", International Journal of Disaster Risk Reduction, vol. 41, © 2019, Elsevier Ltd., 13 pages.*
International Search Report, PCT/CN2023/105651, mailed Oct. 13, 2023. 5 pages.
Office Action, issued by The State Intellectual Property Office of People's Republic of China, CN App. 202210805597.1, issued Aug. 31, 2023, 11 pages.

* cited by examiner

200

Device for helping the operator to question the help-seeker

210 First reference group acquisition module

220 Classification test module

230 Receiver operating characteristic curve acquisition module

240 Candidate question semantic meaning acquisition module

250 Target question semantic meaning acquisition module

SYSTEM FOR HELPING OPERATOR TO QUESTION HELP-SEEKER

CROSS-REFERENCE TO RELATED APPLICATION

This patent application is a national stage of International Application No. PCT/CN2023/105651, filed on Jul. 4, 2023, which claims all the benefits of Patent Application No. 202210805597.1 filed with the China National Intellectual Property Administration on Jul. 8, 2022 and entitled “SYSTEM FOR HELPING OPERATOR TO QUESTION HELP-SEEKER”. Both of the aforementioned applications are hereby incorporated by reference in their entireties.

TECHNICAL FIELD

The present disclosure relates to the technical field of computers, and in particular to a system for helping an operator to question a help-seeker. The present disclosure also relates to a system for helping an operator to determine whether a person to be rescued is a positive example. The present disclosure also relates to a system for helping an investigator to question a respondent. The present disclosure also relates to a system for helping an investigator to determine whether a respondent is a positive example.

BACKGROUND

Out-of-Hospital Cardiac Arrest (OHCA) is the most serious clinical symptom that occurs outside the hospital. Once it happens, patients can die quickly. The golden time for rescue after cardiac arrest lasts only 3-5 minutes, while the average response time of ambulances in China is generally more than 15 minutes. On-site Cardiopulmonary Resuscitation (CPR) is the only hope for OHCA patients to survive.

In recent years, it has been attempted at home and abroad that a dispatcher of an emergency medical dispatching center (for example, 1-2-0 in China) encourages and guides a help-seeker (a telephone caller) or other on-site personnel to provide on-site CPR (that is, telecommunicator CPR) for OHCA patients by telephone when receiving the call for help. For dispatchers who do not have rich emergency professional knowledge, the implementation rate and the success rate of telecommunicator CPR are low, and it is easy to result in patients with OHCA missed. Therefore, how to help the dispatcher to question the help-seeker and how to provide reference data for the dispatcher to help him to determine the on-site situation of the person to be rescued (for example, whether the person to be rescued is a suspected OHCA patient) and the progress of the help-seeker or other on-site personnel in rescuing the person to be rescued (for example, whether the help-seeker has started CPR, used an Automated External Defibrillator (AED), and realized Return Of Spontaneous Circulation (ROSC) after CPR) are technical problems to be solved urgently.

SUMMARY

The embodiment of the present disclosure provides a system for helping an operator to question a help-seeker, which is used for helping a dispatcher to question the help-seeker, so as to help the dispatcher to determine the on-site situation of the person to be rescued (for example, whether the person to be rescued is a suspected OHCA patient) and the progress of the help-seeker or other on-site personnel in rescuing the person to be rescued (for example, whether the help-seeker has started CPR, used an AED, and realized ROSC after CPR). The embodiment of the present disclosure further provides a system for determining a positive probability of a person to be rescued, which is used to provide reference data for the dispatcher, so as to help the dispatcher to determine the on-site situation of the person to be rescued (for example, whether the person to be rescued is a suspected OHCA patient) and the progress of the help-seeker or other on-site personnel in rescuing the person to be rescued (for example, whether the help-seeker has started CPR, used an AED, and realized ROSC after CPR).

One embodiment of the present disclosure provides a system for helping an operator to question a help-seeker, including: a first reference group acquisition module, a classification test module, a receiver operating characteristic curve acquisition module, a candidate question semantic meaning acquisition module and a target question semantic meaning acquisition module; wherein the first reference group acquisition module is configured to select a plurality of first reference groups unprocessed from an initial reference group; wherein the first reference group is obtained by classifying a plurality of historical people to be rescued amongst the initial reference group according to an entity attribute cluster, the entity attribute cluster consists of a plurality of entity attribute pairs corresponding to the same core question, each entity attribute pair includes an entity and attribute, the entity represents the semantic meaning of a question from the operator in a historical call for help, and the attribute represents the semantic meaning of an answer to the question from a help-seeker; the classification test module is configured to set a positive probability of any second reference group included in any first reference group amongst the plurality of first reference groups as a cut-off point, and perform a classification test on any first reference group to obtain a classification sensitivity and a classification specificity corresponding to any second reference group; wherein the cut-off point is used to determine a positive label of the first reference group, and the second reference group is obtained by classifying the first reference group according to the entity attribute; the receiver operating characteristic curve acquisition module is configured to obtain a receiver operating characteristic curve corresponding to any first reference group based on the classification sensitivities and the classification specificities corresponding to a plurality of second reference groups amongst any first reference group; the candidate question semantic meaning acquisition module is configured to determine a target first reference group from the plurality of first reference groups according to the receiver operating characteristic curve corresponding to each first reference group amongst the plurality of first reference groups, and set the entity of each entity attribute pair in the entity attribute cluster corresponding to the target first reference group as a candidate question semantic meaning; and the target question semantic meaning acquisition module is configured to determine a target question semantic meaning from the candidate question semantic meaning according to a distance between a coordinate point corresponding to any second reference group amongst the plurality of second reference groups and a perfect classification coordinate point in the receiver operating characteristic curve corresponding to the target first reference group; wherein the perfect classification coordinate point is a coordinate point with abscissa of 0 and ordinate of 1 in the receiver operating characteristic curve, and the target question semantic meaning is used to help the operator to conduct a next round of question.

In some embodiments, setting the positive probability of any second reference group included in any first reference group amongst the plurality of first reference groups as the cut-off point, and performing the classification test on any first reference group to obtain the classification sensitivity and the classification specificity corresponding to any second reference group includes:

setting members of the second reference group in the first reference group whose positive probability is greater than or equal to the cut-off point as predefined positive examples, and setting members of the second reference group in the first reference group whose positive probability is less than the cut-off point as predefined negative examples; obtaining the classification sensitivity according to the number of members who are truly classified as positive examples in the predefined positive examples and the number of members who are truly classified as positive examples in the first reference group; and obtaining the classification specificity according to the number of members who are truly classified as negative examples in the predefined negative examples and the number of members who are truly classified as negative examples in the first reference group.

In some embodiments, obtaining the receiver operating characteristic curve corresponding to any first reference group based on the classification sensitivities and the classification specificities corresponding to the plurality of second reference groups amongst any first reference group includes: setting the classification sensitivity of any second reference group amongst the plurality of second reference groups as the ordinate and an absolute value of a difference between the classification specificity of any second reference group and 1 as the abscissa, to obtain coordinate points corresponding to any second reference group; and connecting the coordinate points corresponding to each second reference group in the first reference group to obtain the receiver operating characteristic curve corresponding to any first reference group.

In some embodiments, determining the target first reference group from the plurality of first reference groups according to the receiver operating characteristic curve corresponding to each first reference group amongst the plurality of first reference groups includes: calculating an area under curve of the receiver operating characteristic curve corresponding to each first reference group in the plurality of first reference groups; and setting the first reference group corresponding to the maximum area under curve as the target first reference group.

In some embodiments, determining the target question semantic meaning from the candidate question semantic meaning according to the distance between coordinate point corresponding to any second reference group amongst the plurality of second reference groups and the perfect classification coordinate point in the receiver operating characteristic curve corresponding to the target first reference group includes: calculating a plurality of distances between coordinate points corresponding to respective second reference groups in the plurality of second reference groups and the perfect classification coordinate point; and setting the second reference group corresponding to the shortest distance amongst the plurality of distances as a target second reference group, and setting the entity of the entity attribute pair corresponding to the target second reference group as the target question semantic meaning.

In some embodiments, the initial reference group is obtained by: extracting personal characteristic information of a person to be rescued from a help-seeking sentence of the help-seeker, and determining the initial reference group according to the personal characteristic information.

One embodiment of the present disclosure provides a system for helping an operator to determine whether a person to be rescued is a positive example, including: an entity attribute cluster and entity attribute pair determining module, a first reference group and second reference group determining module, a module for acquiring a number of members of predefined positive examples, and a positive probability determining module. The entity attribute cluster and entity attribute pair determining module is configured to determine an entity attribute cluster currently corresponding to the person to be rescued and an entity attribute pair currently corresponding to the person to be rescued according to a question from the operator and an answer to the question from a help-seeker in any round of dialogue between the operator and the help-seeker; wherein the entity attribute cluster consists of a plurality of entity attribute pairs corresponding to the same core question, each entity attribute pair includes an entity and an attribute, the entity represents the semantic meaning of the question from the operator in a historical call for help, and the attribute represents the semantic meaning of the answer to the question from the help-seeker; the first reference group and second reference group determining module is configured to acquire a first reference group corresponding to the entity attribute cluster and a second reference group corresponding to the entity attribute pair from an initial reference group; wherein the first reference group is obtained by classifying a plurality of historical people to be rescued amongst the initial reference group according to the entity attribute cluster, and the second reference group is obtained by classifying the first reference group according to the entity attribute; the module for acquiring a number of members of predefined positive examples is configured to set the positive probability of the second reference group as a cut-off point to obtain the number of members of the first reference group who are predefined positive examples; wherein the cut-off point is configured to determine the positive label of the first reference group; and the positive probability determining module is configured to obtain the positive probability of the person to be rescued according to a ratio between the number of members who are truly classified as positive examples amongst the members of the first reference group who are predefined positive examples and the number of members of the first reference group who are predefined positive examples; wherein the positive probability is used to help the operator to determine whether a person to be rescued is a positive example.

In some embodiments, the system further includes a positive probability trend scatter plot acquisition module and a linear regression equation slope acquisition module; wherein the positive probability trend scatter plot acquisition module is configured to obtain a positive probability trend scatter plot according to a plurality of positive probabilities of the person to be rescued obtained in a plurality of rounds of dialogues between the operator and the help-seeker; and the linear regression equation slope acquisition module is configured to fit the positive probability trend scatter plot by using a linear regression equation and solve the linear regression equation to obtain a linear regression equation slope; wherein the positive probability trend scatter plot and the linear regression equation slope are used to represent a probability trend that the person to be rescued is the positive example.

In some embodiments, obtaining the positive probability trend scatter plot according to the plurality of positive probabilities of the person to be rescued obtained in the plurality of rounds of dialogues between the operator and the help-seeker includes: setting the rounds of the dialogue corresponding to any positive probability amongst the plurality of positive probabilities as the abscissa and the any positive probability as the ordinate to obtain the coordinates on the positive probability trend scatter plot. In some embodiments, determining the entity attribute cluster currently corresponding to the person to be rescued and the entity attribute pair currently corresponding to the person to be rescued includes: acquiring the question from the operator, and extracting question semantic meaning information from the question; acquiring the answer to the question from the help-seeker, and extracting answer semantic meaning information from the answer; determining a core question described in the question, and obtaining the entity attribute cluster according to the core question; and determining the entity attribute pair according to the question semantic meaning information and the answer semantic meaning information.

In some embodiments, setting the positive probability of the second reference group as the cut-off point to obtain the number of members of the first reference group who are predefined positive examples includes: setting the number of members of the second reference group in the first reference group, whose positive probability is greater than or equal to the cut-off point as the number of members of the predefined positive examples.

In some embodiments, the system further includes a rate ratio acquisition module and a rate difference acquisition module; wherein the rate ratio acquisition module is configured to obtain a rate ratio according to a ratio between a current positive probability of the person to be rescued and the positive probability of the person to be rescued obtained in the previous round of dialogue; and the rate difference acquisition module is configured to obtain a rate difference according to the difference between the current positive probability of the person to be rescued and the positive probability of the person to be rescued obtained in the previous round of dialogue; wherein the rate difference and the rate ratio are used to help the operator to determine the value of the current positive probability of the person to be rescued in determining whether the person to be rescued is a positive example.

One embodiment of the present disclosure provides a system for helping an investigator to question a respondent, including: a first reference group acquisition module, a classification test module, a receiver operating characteristic curve acquisition module, a candidate question semantic meaning acquisition module and a target question semantic meaning acquisition module; wherein the first reference group acquisition module is configured to select a plurality of first reference groups unprocessed from an initial reference group; wherein the first reference group is obtained by classifying a plurality of historical respondents amongst the initial reference group according to an entity attribute cluster, the entity attribute cluster consists of a plurality of entity attribute pairs corresponding to the same core question, each entity attribute pair includes an entity and an attribute, the entity represents the semantic meaning of a question from the investigator in a historical call for investigation, and the attribute represents the semantic meaning of an answer to the question from the respondent; the classification test module is configured to set the positive probability of any second reference group included in any first reference group amongst the plurality of first reference groups as a cut-off point, and perform a classification test on any first reference group to obtain a classification sensitivity and a classification specificity corresponding to any second reference group; wherein the cut-off point is used to determine a positive label of the first reference group, and the second reference group is obtained by classifying the first reference group according to the entity attribute; the receiver operating characteristic curve acquisition module is configured to obtain a receiver operating characteristic curve corresponding to any first reference group based on the classification sensitivities and the classification specificities corresponding to a plurality of second reference groups amongst any first reference group; the candidate question semantic meaning acquisition module is configured to determine a target first reference group from the plurality of first reference groups according to the receiver operating characteristic curve corresponding to each first reference group amongst the plurality of first reference groups, and set the entity of each entity attribute pair in the entity attribute cluster corresponding to the target first reference group as a candidate question semantic meaning; and the target question semantic meaning acquisition module is configured to determine a target question semantic meaning from the candidate question semantic meaning according to the distance between a coordinate point corresponding to any second reference group amongst the plurality of second reference groups and a perfect classification coordinate point in the receiver operating characteristic curve corresponding to the target first reference group; wherein the perfect classification coordinate point is a coordinate point with the abscissa of 0 and the ordinate of 1 in the receiver operating characteristic curve, and the target question semantic meaning is used to help the investigator to conduct a next round of question.

One embodiment of the present disclosure provides a system for helping an investigator to determine whether a respondent is a positive example, including: an entity attribute cluster and entity attribute pair determining module, a first reference group and second reference group determining module, a module for acquiring a number of members of predefined positive examples, and a positive probability determining module; wherein the entity attribute cluster and entity attribute pair determining module is configured to determine an entity attribute cluster currently corresponding to the respondent and the entity attribute pair currently corresponding to the respondent according to a question from the investigator and an answer to the question from the respondent in any round of dialogue between the investigator and the respondent; wherein the entity attribute cluster consists of a plurality of entity attribute pairs corresponding to the same core question, each entity attribute pair includes an entity and an attribute, the entity represents the semantic meaning of the question from the investigator in a historical call for investigation, and the attribute represents the semantic meaning of the answer to the question from the respondent; the first reference group and second reference group determining module is configured to acquire a first reference group corresponding to the entity attribute cluster and a second reference group corresponding to the entity attribute pair from an initial reference group; wherein the first reference group is obtained by classifying a plurality of historical respondents amongst the initial reference group according to the entity attribute cluster, and the second reference group is obtained by classifying the first reference group according to the entity attribute; the module for acquiring a number of members of predefined positive examples is configured to set the positive probability of the second reference group as a cut-off point to obtain the number of members of the first reference group who are predefined positive examples; wherein the cut-off point is used to determine the positive label of the first reference group; and the positive probability determining module is configured to obtain the positive probability of the respondent according to the ratio between the number of members who are truly classified as positive examples amongst the members of the first reference group who are predefined positive examples and the number of members of the first reference group who are predefined positive examples; wherein the positive probability is used to help the investigator to determine whether the respondent is the positive example.

In the embodiment provided by the present disclosure, the entity attribute cluster consists of entity attribute pairs with the same theme in the historical call for help, and the entity attribute pair consists of the question semantic meaning of the operator and the answer semantic meaning of the help-seeker, so that a large number of disordered historical dialogues in a call-for-help dispatching database are structured. In this way, the historical person to be rescued can be classified through the historical dialogues to obtain a first reference group and a second reference group. According to the embodiment provided by the present disclosure, a classification test is performed on the first reference group by setting the positive probability of any second reference group as the cut-off point, so that the second reference group obtained according to the classification of the entity attribute pair can be continuously divided. In this way, the first reference group obtained according to the classification of the entity attribute cluster is computable, and the classification sensitivity and the classification specificity obtained by setting the positive probability of the second reference group as the cut-off point can accurately reflect the effectiveness of the dialogue represented by the entity attribute pair corresponding to the second reference group in determining the on-site situation of the person to be rescued and the progress of the help-seeker of rescuing the person to be rescued.

In the embodiment provided by the present disclosure, the receiver operating characteristic curve corresponding to the first reference group is obtained based on the classification sensitivity and the classification specificity corresponding to any second reference group. The effectiveness of a plurality of entity attribute clusters in determining the on-site situation of the person to be rescued and the progress of the help-seeker of rescuing the person to be rescued can be quantified, so that the core problems represented by the entity attribute cluster that is helpful to determining the on-site situation of the person to be rescued and the progress of the help-seeker of rescuing the person to be rescued can be obtained.

In the embodiment provided by the present disclosure, the effectiveness of the entity attribute pair in determining the on-site situation of the person to be rescued and the progress of the help-seeker of rescuing the person to be rescued can be quantified by calculating the obtained distance between a coordinate point corresponding to any second reference group amongst the plurality of second reference groups and a perfect classification coordinate point in the receiver operating characteristic curve corresponding to the target first reference group, so that the question semantic meaning represented by the entity attribute pair that is helpful to determining the on-site situation of the person to be rescued and the progress of the help-seeker of rescuing the person to be rescued can be obtained.

According to the embodiment provided by the present disclosure, the entity attribute cluster currently corresponding to the person to be rescued and the entity attribute pair currently corresponding to the person to be rescued is determined according to a question from an operator and an answer to the question from the help-seeker. A first reference group corresponding to the entity attribute cluster and a second reference group corresponding to the entity attribute pair is acquired from an initial reference group, so that the historical reference group of the person to be rescued can be obtained through dialogues. According to the embodiment provided by the present disclosure, the positive probability of the second reference group is taken as a cut-off point to obtain the number of members of the first reference group who are predefined positive examples, and then the positive probability of the person to be rescued is obtained according to the ratio between the number of members who are truly classified as positive examples amongst the members of the first reference group who are predefined positive examples and the number of members of the first reference group who are predefined positive examples, so that the patient medical record resources in a call-for-help dispatching database are made full use of, and the probability that a person to be rescued is a positive example can be obtained more accurately through the dialogue between the operator and the help-seeker.

BRIEF DESCRIPTION OF THE DRAWINGS

The present disclosure will be further illustrated by way of exemplary embodiments, which will be described in detail with the attached drawings. These embodiments are not limiting, and in these embodiments, the same reference numerals refer to the same structures, and in which.

DETAILED DESCRIPTION OF THE EMBODIMENTS

Figures 1, 2:
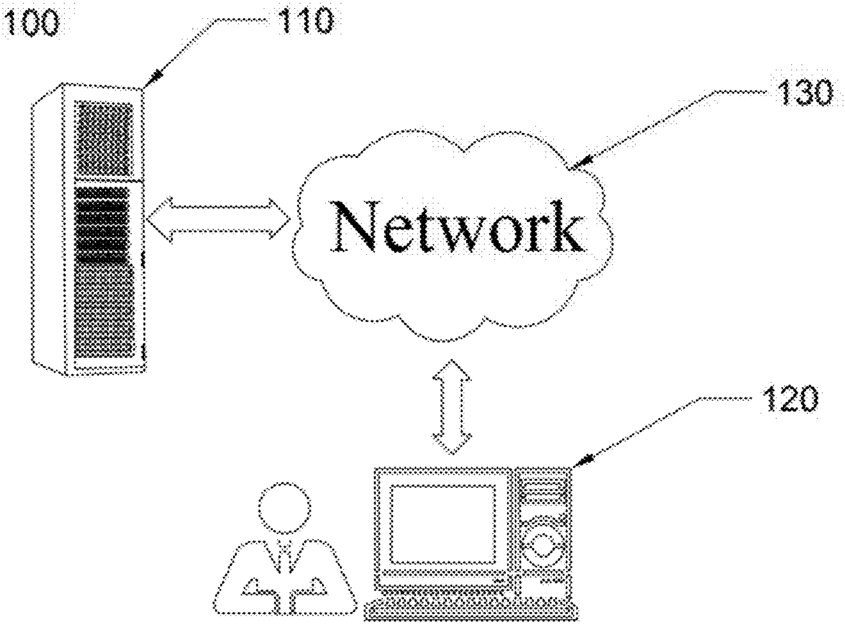
FIG. 1 is a schematic diagram of an application scenario of a system for helping an operator to question a help-seeker and a system for helping an operator to determine whether a person to be rescued is a positive example according to some embodiments of the present disclosure.
FIG. 2 is an exemplary schematic diagram of a system for helping an operator to question a help-seeker according to some embodiments of the present disclosure.

In order to explain the technical scheme of the embodiment of the present disclosure more clearly, the attached drawings needed in the description of the embodiment will be briefly introduced hereinafter. Obviously, the attached drawings in the following description are only some examples or embodiments of the present disclosure. For those skilled in the art, the present disclosure can be applied to other similar situations according to these attached drawings without creative labor. Unless it is obvious from the linguistic context or otherwise stated, the same reference numerals in the attached drawings refer to the same structure or operation.

It should be understood that "system", "device", "unit" and/or "module" as used herein is a method for distinguishing different components, elements, parts, portions or assemblies at different levels. However, if other words can achieve the same purpose, the words can be replaced by other expressions.

As shown in the present disclosure and claims, unless the context clearly indicates an exception, the words "a", "an", "one" and/or "the" do not refer to the singular, but may also include the plural. Generally speaking, the terms "including" and "containing" only imply the inclusion of clearly identified steps and elements, and these steps and elements do not constitute an exclusive list, and a method or a device may also include other steps or elements.

Flowcharts are used in the present disclosure to explain the operations performed by the system according to the embodiment of the present disclosure. It should be understood that the preceding or following operations are not necessarily performed accurately in order. Instead, the steps can be processed in reverse order or simultaneously. At the same time, other operations can be added to these processes, or one or more steps can be removed from these processes.

FIG. 1 is a schematic diagram of an application scenario of a system for helping an operator to question a help-seeker and a system for helping an operator to determine whether a person to be rescued is a positive example according to some embodiments of the present disclosure.

The system for helping the operator to question the help-seeker and the system for helping the operator to determine whether a person to be rescued is a positive example provided by the embodiment of the present disclosure can be applied to various task scenarios, such as the call rescue scene of the emergency medical dispatching center, the call recommendation scenario of the online sales platform and the like. For example, the online platform can use the system provided by the present disclosure to obtain the target question semantic meaning for helping the operator to conduct the next round of question, and the operator can refer to the target question semantic meaning to determine the real purchase intention of the call consultation user through questioning.

Just as an example, the application scenario of the system for helping the operator to question the help-seeker in the present disclosure will be described hereinafter by taking the call rescue task of the emergency medical dispatching center as an example.

As shown in FIG. 1, an application scenario 100 may include a server 110, a terminal 120 and a network 130.

In some embodiments, data or information can be exchanged between the server 110 and the terminal 120 through the network 130. For example, the server 110 can acquire information and/or data in the terminal 120 through the network 130, or can send the information and/or data to the terminal 120 through the network 130.

The terminal 120 is an electronic device used by an operator (for example, a dispatcher of an emergency medical dispatching center) to answer a call for help, and the call emergency guidance can be provides to the operator through the terminal 120. In some embodiments, the terminal 120 can acquire the question from the operator and the answer from the help-seeker, and send the question and the answer to the server 110 for processing. In some embodiments, the terminal 120 can display the target question semantic meaning, the positive probability of the person to be rescued, the rate ratio, the rate difference and the positive probability trend scatter plot received from the server 110 to the operator in various ways (for example, voice prompt, text prompt, etc.). In some embodiments, when the processing capacity of the terminal 120 is high, the terminal 120 can also process the question from the operator and the answer from the help-seeker to obtain the target question semantic meaning, the positive probability of the person to be rescued, the rate ratio, the rate difference and the positive probability trend scatter plot, which is not limited by the description in this specification. The terminal 120 can be one or any combination of devices with input and/or output functions such as mobile devices and tablet computers.

The server 110 may be a single server or a group of servers. The group of servers can be centralized or distributed (for example, the server 110 can be a distributed system), can be dedicated or can be served by other devices or systems at the same time. In some embodiments, the server 110 may be local or remote. In some embodiments, the server 110 may be implemented on a cloud platform or provided in a virtual way. As an example only, the cloud platform may include a private cloud, a public cloud, a hybrid cloud, a community cloud, a distributed cloud, an internal cloud, a multi-tier cloud, etc., or any combination thereof.

In some embodiments, the server 110 can maintain the call-for-help dispatching database of the emergency center, and classify patients in the dispatching database according to the entity attribute cluster and the entity attribute pair. In some embodiments, the server 110 can obtain the first reference group and the second reference group that need to participate in the operation from the call-for-help dispatching database according to the question between the operator and the help-seeker, and send the data information of the first reference group or the second reference group to the terminal 120.

In some embodiments, the network 130 may be any one or more of a wired network or a wireless network. For example, the network 130 may include a local area network (LAN), a wide area network (WAN), a wireless local area network (WLAN), a metropolitan area network (MAN), etc., or any combination thereof.

In order to facilitate understanding, the technical scheme of the present disclosure is introduced in conjunction with the attached drawings and embodiments hereinafter.

FIG. 2 is an exemplary schematic diagram of a system for helping an operator to question a help-seeker according to some embodiments of the present disclosure. As shown in FIG. 2, the system for helping the operator to question the help-seeker includes a first reference group acquisition module 210, a classification test module 220, a receiver operating characteristic curve acquisition module 230, a candidate question semantic meaning acquisition module 240 and a target question semantic meaning acquisition module 250.

Figure 4:
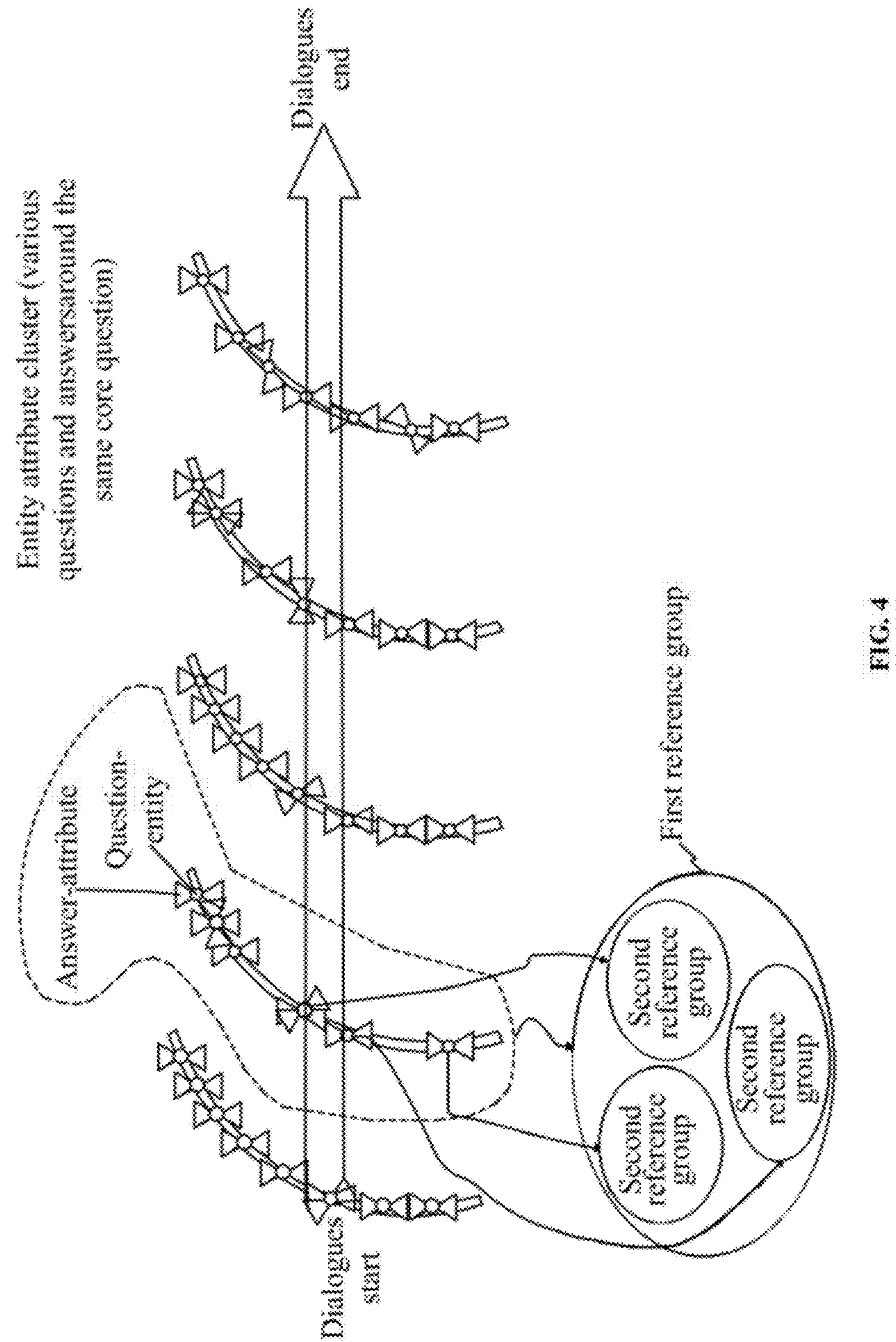
FIG. 4 is an exemplary schematic diagram of an entity attribute cluster, an entity attribute pair, a first reference group and a second reference group according to some embodiments of the present disclosure.

The first reference group acquisition module 210 is configured to select a plurality of first reference groups unprocessed from an initial reference group. The first reference group is obtained by classifying a plurality of historical people to be rescued (for example, suspected OHCA patients) amongst the initial reference group according to an entity attribute cluster. The entity attribute cluster consists of a plurality of entity attribute pairs corresponding to the same core question. The core problem is the theme that the operator tries to understand through questioning. For example, the core questions can be: help, consciousness, breathing, heart, talking and other topics. The entity attribute pairs include entities and attributes. The entity represents the semantic meaning of a question from an operator in a historical call for help, and the attribute represents the semantic meaning of an answer to the question from a help-seeker. For example, for the question "Hello, what can I do for you?" from the operator and the answer "Not good, my father is dying" from the help-seeker, the semantic meaning "Hello" is extracted from the question, the semantic meaning "dying" is extracted from the answer. Therefore, the entity attribute pair corresponding to the question and answer is: "Hello-dying". Because the core question of the question is "help", the entity attribute pair corresponding to the question and the answer belongs to the "help" entity attribute cluster. As shown in FIG. 4, the question and the answer based on the same core question constitute an entity attribute cluster, and different entity attribute clusters are independent of each other. The seats (solid points) on the entity attribute cluster represent entities extracted from the core question, and each entity corresponds to at least one different attribute, and the entity and the attribute together constitute an entity attribute pair.

In the specific implementation process, all dialogues between the operator and the help-seeker can be converted into a text by using an audio-to-text algorithm, and then text recognition can be carried out on the converted text to obtain questions and answers represented in words. In some embodiments, the questions and answers in words can be stored in different databases. In the process of calling for help by a help-seeker, the questions and answers are recalled from the question database and the answer database, respectively, and the questions and answers are matched to obtain the entity attribute clusters and the entity attribute pairs corresponding to the dialogue.

There are a large number of disordered emergency dialogues stored in the call-for-help dispatching database, which is difficult to be standardized and structured. Therefore, it is difficult to use the dialogues to detect an emergent case such as cardiac arrest. According to the embodiment provided by the present disclosure, the emergency dialogue in the call-for-help dispatching database is structured through the concepts of the entity attribute cluster and the entity attribute pair, so that the existing dialogue data resources can be used to guide the dispatcher to question the help-seeker to determine the on-site situation of the person to be rescued and the progress of the help-seeker in rescuing the person to be rescued, thereby reducing the requirements for the professionalism of the emergency dispatcher and enabling an ordinary dispatcher to provide effective emergency services for patients.

The initial reference group is a group of historical people to be rescued selected from the call-for-help dispatching database. In the specific implementation process, the personal characteristic information of the person to be rescued can be extracted from a help-seeking sentence of the help-seeker, and the initial reference group can be determined from the database (for example, the call-for-help dispatching database) according to the personal characteristic information. The personal characteristic information includes, but is not limited to, information indicating the personal characteristics of the person to be rescued such as gender, age, body shape, time of calling for help, and geographical location. For example, for the following dialogue scenario, the operator asks, "Hello, xxx Command Center, how can I help you?", the help-seeker answers "Not good, my father is dying", two pieces of characteristic information of "adult" and "male" can be extracted from the semantic meaning of the answer from help-seeker, and 500,000 historical people to be rescued who satisfy the characteristic information can be selected from the database as the initial reference group. With the progress of the dialogue, the reference group with more similar situation to the person to be rescued can be obtained from the database according to the entity attribute cluster and the entity attribute pair corresponding to each round of dialogue.

The initial reference group can be further divided into a plurality of first reference groups according to entity attribute clusters. For example, the initial reference group can include: the first reference group corresponding to the "help" entity attribute cluster, the first reference group corresponding to the "consciousness" entity attribute cluster, and the first reference group corresponding to the "breathing" entity attribute cluster, etc.

In the specific implementation process, a plurality of first reference groups unprocessed can be selected from the initial reference group, and then based on the plurality of first reference groups, the target question semantic meaning for helping the operator to conduct the next round of question can be obtained. Just as an example, the entity attribute cluster corresponding to the current dialogue is a "help" entity attribute cluster, and the initial reference group further includes first reference groups unprocessed corresponding to four entity attribute clusters. For the convenience of description, the four entity attribute clusters are named as a consciousness cluster, a breathing cluster, a heart cluster and a talking cluster, so that the first reference group corresponding to the consciousness cluster, the first reference group corresponding to the breathing cluster, the first reference group corresponding to the heart cluster and the first reference group corresponding to the talking cluster can be selected as the plurality of first reference groups for subsequent processing.

The classification test module 220 is configured to take the positive probability of any second reference group included in any first reference group amongst the plurality of first reference groups as a cut-off point, and perform a classification test on any first reference group to obtain a classification sensitivity and a classification specificity corresponding to any second reference group.

As shown in FIG. 4, the second reference group is obtained by classifying the first reference group according to the entity attribute. For example, the consciousness cluster in the above example includes four entity attribute pairs (the number of entity attribute pairs actually contained may be much larger than four, which is simplified for the convenience of description): "coma-yes", "reaction-shock", "wakefulness-no reaction" and "reaction-immobility", and then the first reference group corresponding to the consciousness cluster can be divided into four second reference groups according to these four entity attribute pairs. For another example, the posture guidance cluster (entity attribute cluster) includes four entity attribute pairs (the number of entity attribute pairs actually contained may be much larger than four, which is simplified for the convenience of description): "lying flat-keeping flat", "leaning back-well now", "lying flat-yes" and "lying supine-OK", and then first reference group corresponding to the posture guidance cluster can be divided into four second reference groups according to these four entity attribute pairs.

The positive probability of the second reference group can be the ratio of the members who are truly classified as positive examples to the total number of people in the second reference group, which is expressed by the calculation formula as follows:

$P_c$=the number of patients who are truly classified as positive examples/the total number of people     Formula (1)

Just as an example, the total number of people of a certain second reference group is 100,000, amongst which 5000 members are confirmed as positive examples, and thus the positive probability of the second reference group is 0.005.

The positive examples, also known as "positive instances", are appropriate instances or examples of concepts. All positive examples of every concept contain common essential features, and every concept has positive examples and negative examples (negative instances). For example, elephants, lions, tigers, cats, dogs and whales are positive examples of the concept of mammals, while fish and turtles are negative examples of the concept of mammals.

In the scenario of the call rescue task of the emergency medical dispatching center, when the dispatcher tries to determine whether the patient is in a certain state, the patient in the state is a positive example, and the patient who is not in the state is a negative example. For example, in the case that the dispatcher determines whether the person to be rescued is a suspected OHCA patient through dialogues (because only emergency doctors can diagnose whether the person to be rescued is an OHCA patient, the dispatcher can only judge that the person to be rescued is an OHCA patient), the positive example can be a patient diagnosed as OHCA by an emergency doctor, and the negative example can be a patient diagnosed as non-OHCA by an emergency doctor. For another example, in the case that the dispatcher determines the progress of the help-seeker in rescuing the person to be rescued through dialogues, the positive example can be the patient for whom the help-seeker has started CPR, and the negative example can be the patient for whom the help-seeker has not started CPR. For another example, in the case that the dispatcher determines whether the person to be rescued has realized ROSC through dialogues, the positive example can be the patient who has realized ROSC, and the negative example can be the patient who has not realized ROSC.

In other application scenarios, positive examples or negative examples can refer to different object groups from the positive examples or negative examples in the call rescue task scenario of the emergency medical dispatching center, which are not limited by the expression in this specification. For example, in the call recommendation scenario of the online sales platform, the positive example can be the user who has a purchase intention for a certain commodity, and the negative example can be the user who has no purchase intention for a certain commodity.

A predefined positive example is an object that is assumed to be a positive example, that is, the true classification of a predefined positive example may be a positive example or a negative example. A predefined negative example is an object that is assumed to be a negative example, that is, the true classification of a predefined negative example may be a negative example or a positive example. In the call rescue task scenario of the emergency medical dispatching center, the predefined positive example is the patient who is assumed to be in a certain state by the system for classification test or other calculation, and the predefined negative example is the patient who is assumed not to be in a certain state by the system for classification test or other calculation. For example, when the dispatcher judges whether the person to be rescued is a suspected OHCA patient through dialogues, the predefined positive example can be a patient who is assumed by the system to be diagnosed as OHCA by a doctor, and the predefined negative example can be a patient who is assumed by the system to be diagnosed as non-OHCA by a doctor. For another example, in the case that the dispatcher determines the progress of the help-seeker in rescuing the person to be rescued through dialogues, the predefined positive example can be the patient for whom the help-seeker has started CPR assumed by the system, and the predefined negative example can be the patient for whom the help-seeker has not started CPR assumed by the system. For another example, in the case that the dispatcher determines whether the person to be rescued has realized ROSC through dialogues, the predefined positive example can be the patient who has realized ROSC assumed by the system, and the predefined negative example can be the patient who has not realized ROSC assumed by the system.

The cut-off point is used to determine a positive label of the first reference group. In some embodiments, the positive probability of the second reference group can be taken as the cut-off point, members of the second reference group in the first reference group whose positive probability is greater than or equal to the cut-off point can be taken as predefined positive examples, and members of the second reference group in the first reference group whose positive probability is less than the cut-off point can be taken as predefined negative examples.

For example, the "help" entity attribute cluster contains four entity attribute pairs (the number of entity attribute pairs actually included may be much larger than four, which is simplified for the convenience of description): "Hello-fainting", "Hello-dying", "Hello-coming quickly" and "Hello-ambulance". After being ranked, the positive probability of the second reference group corresponding to each entity attribute pair is: P=0.165 (Hello-fainting), P=0.035 (Hello-dying), P=0.019 (Hello-coming quickly) and P=0.011 (Hello-ambulance), respectively. If P=0.035 (Hello-dying) is taken as the cut-off point, the members (whose positive probability is 0.165 greater than the cut-off point 0.035) of the second reference group corresponding to the "Hello-fainting" entity attribute pair and the members (whose positive probability is 0.035 equal to the cut-off point 0.035) of the second reference group corresponding to the "Hello-dying" entity attribute pair can be taken as predefined positive examples. The members (whose positive probability is 0.019 less than the cut-off point 0.035) of the second reference group corresponding to the "Hello-coming quickly" entity attribute pair and the members (whose positive probability is 0.011 less than the cut-off point 0.035) of the second reference group corresponding to the "Hello-ambulance" entity attribute pair are taken as predefined negative examples.

For another example, the palm positioning cluster (entity attribute cluster) contains four entity attribute pairs (the number of entity attribute pairs actually included may be much larger than four, which is simplified for the convenience of description): "Put your hands together and put your palms in the center of the nipples of the patient-OK", "Put your palms in the center of the nipples of the patient-OK", "Put your hands together and put them on the chest of the patient-OK", and "Put your hands on the chest of the patient-OK". After being ranked, the positive probability of the second reference group corresponding to each entity attribute pair is: P=0.857 (Put your hands together and put your palms in the center of the nipples of the patient-OK), P=0.811 (Put your palms in the center of the nipples of the patient-OK), P=0.789 (Put your hands together and put them on the chest of the patient-OK) and P=0.667 (Put your hands on the chest of the patient-OK). If P=0.811 (Put your palms in the center of the nipples of the patient-OK) as the cut-off point, the members (whose positive probability is greater than the cut-off point) of the second reference group corresponding to the "Put your hands together and put your palms in the center of the nipples of the patient-OK" entity attribute pair and the members (whose positive probability is equal to the cut-off point) of the second reference group corresponding to the "Put your palms in the center of the nipples of the patient-OK" entity attribute pair can be taken as predefined positive examples. The members (whose positive probability is less than the cut-off point) of the second reference group corresponding to the "Put your hands together and put them on the chest of the patient-OK" entity attribute pair and the members (whose positive probability is less than the cut-off point) of the second reference group corresponding to the "Put your hands on the chest of the patient-OK" entity attribute pair can be taken as predefined negative examples.

Classification tests can include screening tests and diagnostic tests, and those unidentified suspected patients can be found in seemingly healthy people by using rapid and simple experimental examinations or other means. In the call rescue scene of the emergency medical dispatching center, the dispatcher determines the real disease state of the person to be rescued through the dialogue with the help-seeker. Usually, it is necessary to calculate the classification sensitivity and the classification specificity to evaluate the authenticity of the classification test. The table of the classification test is as follows:

TABLE 1

| Classification test (realized through dialogues) | True classification | |
|---|---|---|
| | Yes (Y = 1) | No (Y = 0) |
| Label (x = 1) | True positive (a) | False positive (b) |
| Negative (x = 0) | False negative (c) | True negative (d) |

In the specific implementation process, the classification sensitivity can be obtained according to the number of members who are truly classified as positive examples (true positive (a) in Table 1) in the predefined positive examples and the number of members who are truly classified as positive examples (the sum of true positive (a) and false negative (c) in Table 1) in the first reference group. The calculation formula is as follows:

$$Se = \frac{a}{a+c} \quad \text{Formula (2)}$$

In the specific implementation process, the classification specificity can be obtained according to the number of members who are truly classified as negative examples (true negative (d) in Table 1) in the predefined negative examples and the number of members who are truly classified as negative examples (the sum of false positive (b) and true negative (d) in Table 1) in the first reference group. The calculation formula is as follows:

$$Sp = \frac{d}{b+d} \quad \text{Formula (3)}$$

As an example only, the breathing cluster includes four entity attribute pairs (the actual number is much greater than four, which is simplified for the convenience of description). After being ranked according to the positive probability of the second reference group, the positive probabilities of second reference group corresponding to each entity attribute pair is: "breathing-none" (P=0.400), "breathing-uncomfortable" (P=0.210), "gasping-suffocating" (P=0.145) and "gasping-very weak" (P=0.074), respectively. According to the above hypothesis, the classification test is carried out on the first reference group corresponding to the "breathing cluster" with the positive probability of the second reference group corresponding to "breathing-none" as the cut-off point, and Table 2 is obtained.

TABLE 2

| Classification test (realized through dialogues) | On-site doctors diagnose OHCA | |
|---|---|---|
| | Yes (Y = 1) | No (Y = 0) |
| Breathing-None (X = 1) | a = 480 | b = 720 |
| Without the label (X = 0) | c = 1120 | d = 12,680 |

In Table 2, X represents the cut-off point, and X=1 represents that the members satisfying the classification conditions of the cut-off point are taken as the predefined positive examples. In this example, the positive probability (0.400) of the second reference group corresponding to "breathing-none" is taken as the cut-off point, the members of the second reference group corresponding to "breathing-none" are taken as the predefined positive examples, and the members (whose the positive probability is less than 0.400) of the second reference groups corresponding to the remaining entity attributes are taken as the predefined negative examples. In Table 2, the number of members of the predefined positive examples who are truly classified as positive examples (a) is 480, the number of members (a+c) of the first reference group who are truly classified as positive examples is $$480 + 1120 = 1600,$$

and according to $$Se = \frac{480}{1600} = 0.300, \quad \text{Formula (2)}$$

can be calculated. The number of members (d) of the predefined negative example who are truly classified as negative examples is 12,680, and the number of members (b+d) of the first reference group who are truly classified as negative examples is $$720 + 12,680 = 13,400,$$

and according to $$Sp = \frac{12680}{13400} = 0.946 \quad \text{Formula (3)}$$

can be calculated.

According to the above method, the positive probabilities of the second reference groups corresponding to "breathing-uncomfortable", "gasping-suffocating" and "gasping-somewhat weak" are taken as the cut-off points, and the classification sensitivity and the classification specificity corresponding to each second reference group can be obtained.

The receiver operating characteristic curve (ROC) acquisition module 230 is configured to obtain an receiver operating characteristic curve corresponding to any first reference group based on the classification sensitivities and the classification specificities corresponding to a plurality of second reference groups amongst any first reference group.

The receiver operating characteristic curve refers to the connecting line of points drawn under specific stimulus conditions with the difference between 1 and the classification specificity (Sp) obtained by subjects under different criteria as the abscissa and with the classification sensitivity (Se) as the ordinate. The characteristic of the receiver operating characteristic curve is that the curve must pass through (0, 0) and (1, 1), and the points on the curve can only appear above the connecting line of the above two points and increase monotonically. Therefore, the receiver operating characteristic curve is meaningful only if AUC>0.5.

Figure 5:
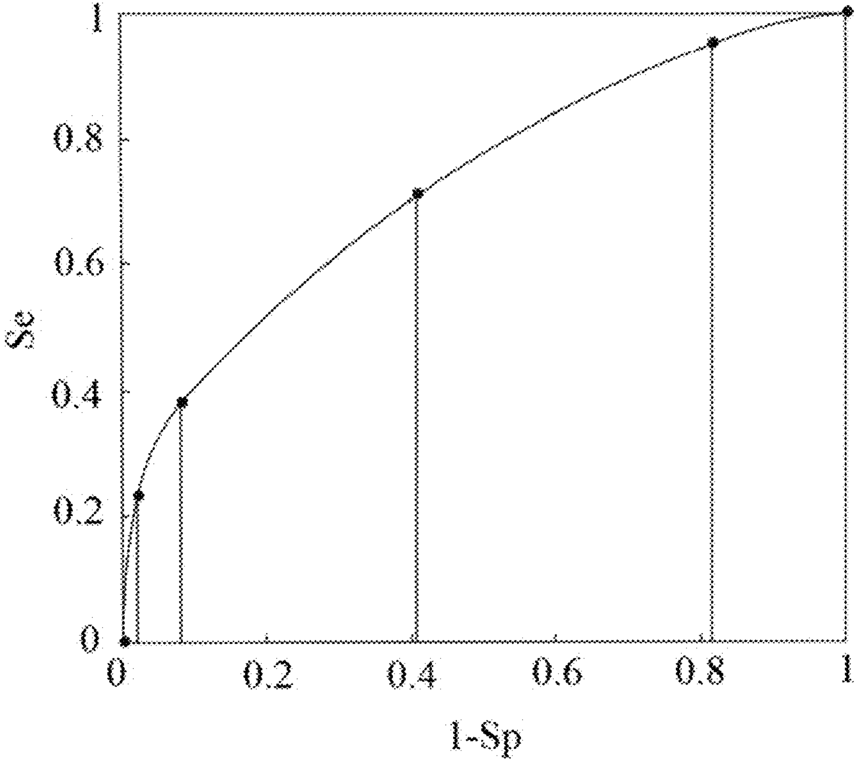
FIG. 5 is an exemplary schematic diagram of a receiver operating characteristic curve according to some embodiments of the present disclosure.

In the specific implementation process, the classification sensitivity of any second reference group amongst the plurality of second reference groups can be taken as the ordinate, the difference between 1 and the classification specificity of any second reference group can be taken as the abscissa to obtain a coordinate point corresponding to any second reference group, and then the coordinate points corresponding to respective second reference groups in the first reference group are connected to obtain the receiver operating characteristic curve corresponding to any first reference group. Just as an example, the receiver operating characteristic curve as shown in FIG. 5 can be obtained by using the classification sensitivities and the classification specificities corresponding to a plurality of second reference groups in the first reference group corresponding to the "breathing cluster" obtained in the above example.

The candidate question semantic meaning acquisition module 240 is configured to determine a target first reference group from the plurality of first reference groups according to the receiver operating characteristic curve corresponding to each first reference group amongst the plurality of first reference groups, and take the entity of each entity attribute pair in the entity attribute cluster corresponding to the target first reference group as a candidate question semantic meaning.

The larger area under curve (AUC) of the receiver operating characteristic curve indicates that the classification effect of the classification test corresponding to the curve is better. Therefore, in some embodiments, the area under curve of the receiver operating characteristic curve corresponding to each first reference group in a plurality of first reference groups can be calculated (for example, by using the trapezoidal rule), and then the first reference group corresponding to the maximum area under curve can be taken as the target first reference group. As an example only, for the three first reference groups corresponding to the entity attribute clusters named "breathing cluster", "heart cluster" and "talking cluster", respectively, the corresponding receiver operating characteristic curves are obtained by using the above method, and the area under curves of the receiver operating characteristic curves are calculated as 0.761, 0.733 and 0.662, respectively, wherein the maximum area under curve corresponds to the first reference group corresponding to the "breathing cluster". Therefore, the first reference group corresponding to the "breathing cluster" is taken as the target first reference group.

After obtaining the target first reference group, the entity of each entity attribute pair in the entity attribute cluster corresponding to the target first reference group can be taken as the candidate question semantic meaning. As an example only, the "breathing cluster" corresponding to the target first reference group obtained in the above example includes the following entity attribute pairs: "breathing-none", "breathing-uncomfortable", "gasping-suffocation" and "gasping-somewhat weak". Therefore, "breathing" and "gasping" can be used as the candidate question semantic meaning. The target question semantic meaning can be selected from the candidate question semantic meaning later.

The target question semantic meaning acquisition module is configured to determine a target question semantic meaning from the candidate question semantic meaning according to the distance between a coordinate point corresponding to any second reference group amongst the plurality of second reference groups and a perfect classification coordinate point in the receiver operating characteristic curve corresponding to the target first reference group.

The perfect classification coordinate point is the coordinate point with the abscissa of 0 and the ordinate of 1 in the receiver operating characteristic curve. The coordinate point (0, 1) in the receiver operating characteristic curve indicates the classification test result with the classification specificity of 1 and the classification sensitivity of 1, which belongs to the perfect result with the highest classification accuracy. In the receiver operating characteristic curve, the distance between the coordinate point corresponding to any second reference group and the perfect classification coordinate point can reflect the accuracy of the classification results obtained by conducting the classification test of the first reference group with the positive probability of any second reference group as the cut-off point. The distance between the coordinate point corresponding to any second reference group and the perfect classification coordinate point in the receiver operating characteristic curve can be obtained by the following formula:

$$d = \sqrt{(1 - Sp)^2 + (1 - Se)^2} \quad \text{Formula (4)}$$

In the specific implementation process, a plurality of distances between coordinate points corresponding to respective second reference groups in the plurality of second reference groups and a perfect classification coordinate point are calculated, and the second reference group corresponding to the shortest distance amongst the plurality of distances is taken as the target second reference group, and the entity of the entity attribute pair corresponding to the target second reference group is taken as the target question semantic meaning. As an example only, the "breathing cluster" corresponding to the target first reference group in the above example includes the following entity attribute pairs: "breathing-none", "breathing-uncomfortable", "gasping-suffocation" and "gasping-somewhat weak". In the receiver operating characteristic curve, the distances from four coordinate points corresponding to the four entity attribute pairs to (0, 1) are 0.702, 0.548, 0.419 and 0.537, respectively. Therefore, "gasping" in "gasping-suffocation" is taken as the target question semantic meaning.

The target question semantic meaning is used to help the operator to conduct the next round of question. In some embodiments, the operator is the dispatcher of the emergency medical dispatching center, and the question from the dispatcher is used to determine whether the person to be rescued needs on-site CPR.

In some embodiments, the operator is the dispatcher of the emergency medical dispatching center, and the question from the dispatcher is used to help the help-seeker to conduct on-site CPR on the person to be rescued.

Figure 3:
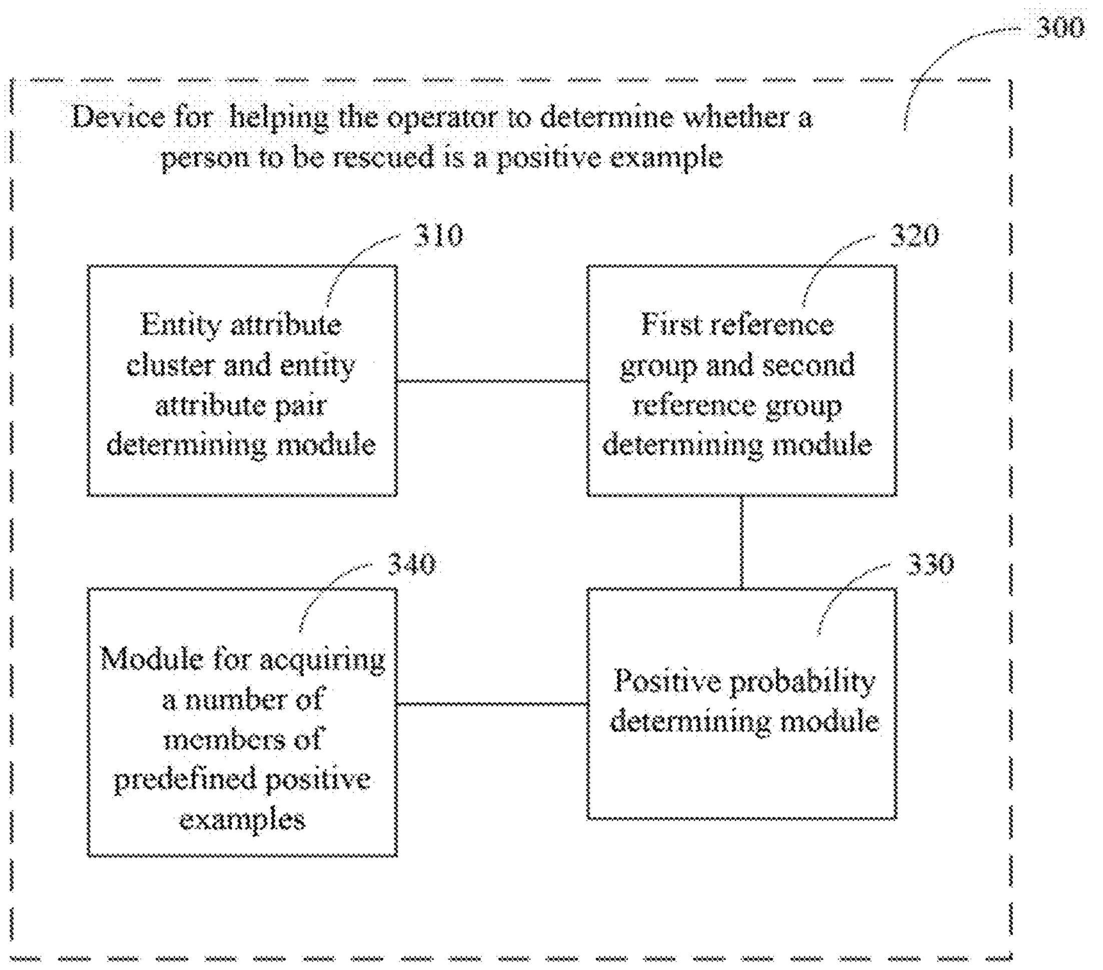
FIG. 3 is an exemplary schematic diagram of a system for helping an operator to determine whether a person to be rescued is a positive example according to some embodiments of the present disclosure.

FIG. 3 is an exemplary schematic diagram of a system for helping an operator to determine whether a person to be rescued is a positive example according to some embodiments of the present disclosure. As shown in FIG. 3, the system for helping the operator to determine whether a person to be rescued is a positive example includes an entity attribute cluster and entity attribute pair determining module 310, a first reference group and second reference group determining module 320, a module for acquiring a number of members of predefined positive examples 330, and a positive probability determining module 340.

The entity attribute cluster and entity attribute pair determining module 310 is configured to determine the entity attribute cluster currently corresponding to the person to be rescued and the entity attribute pair currently corresponding to the person to be rescued according to a question from an operator and an answer to the question from the help-seeker in any round of dialogue between the operator and a help-seeker.

The entity attribute cluster consists of a plurality of entity attribute pairs corresponding to the same core question, each entity attribute pair includes an entity and an attribute, the entity represents the semantic meaning of a question from an operator in a historical call for help, and the attribute represents the semantic meaning of an answer to the question from a help-seeker.

In the specific implementation process, a question from the operator can be acquired, and question semantic meaning information can be extracted from the question. The answer to the question from the help-seeker can be acquired, and answer semantic meaning information can be extracted from the answer. A core question described in the question is determined, and the entity attribute cluster is obtained according to the core question. The entity attribute pair is determined according to the question semantic meaning information and the answer semantic meaning information. For details of the entity attribute clusters and the entity attribute pairs, refer to FIG. 2, which will not be described in detail here.

The first reference group and second reference group determining module 320 is configured to acquire a first reference group corresponding to the entity attribute cluster and a second reference group corresponding to the entity attribute pair from an initial reference group; wherein the first reference group is obtained by classifying a plurality of historical people to be rescued amongst the initial reference group according to an entity attribute cluster, and the second reference group is obtained by classifying the first reference group according to the entity attribute.

For details of the initial reference group, the first reference group and the second reference group, refer to FIG. 2, which will not be described in detail here.

The module for acquiring a number of members of predefined positive examples 330 is configured to take the positive probability of the second reference group as a cut-off point to obtain the number of members of the first reference group who are predefined positive examples.

The cut-off point is used to determine the positive label of the first reference group. For details of the cut-off point, refer to FIG. 2, which will not be described in detail here.

In some embodiments, the number of members of the second reference group in the first reference group whose positive probability is greater than or equal to the cut-off point can be taken as the number of members of the predefined positive examples. For details of this embodiment, refer to the example in Step S220, which will not be described in detail here.

The positive probability determining module 340 is configured to obtain the positive probability of the person to be rescued according to the ratio between the number of members who are truly classified as positive examples amongst the members of the first reference group who are predefined positive examples and the number of members of the first reference group who are predefined positive examples.

As an example only, the "help" entity attribute cluster contains four entity attribute pairs (the number of entity attribute pairs actually included may be much larger than four, which is simplified for the convenience of description. After being ranked according to the positive probability of the second reference group, these four entity attribute pairs and the positive probability of the second reference group corresponding to each entity attribute pair are: "Hello-fainting" (P=0.165), "Hello-dying" (P=0.035), "Hello-coming quickly" (P=0.019) and "Hello-ambulance" (P=0.011). According to the answer "Hello, my dad is dying" from the current help-seeker, and taking the positive probability (0.035) of the second reference group corresponding to "Hello-dying" as the cut-off point, the members in the second reference groups corresponding to the "Hello-fainting" entity attribute pair (the positive probability of the corresponding second reference group is 0.165, which is greater than the cut-off point) and "Hello-dying" entity attribute pair (the positive probability of the corresponding second reference group is 0.035, which is equal to the cut-off point) can be taken as the predefined positive examples, the number of which is 100,000 in total. Among these 100,000 members, there are 4,000 OHCA members diagnosed by doctors, so that the probability of positive examples of the people to be rescued is 0.04.

The positive probability of the person to be rescued is used to help the operator to determine whether a person to be rescued is a positive example. In some embodiments, the operator is the dispatcher of the emergency medical dispatching center, and the positive example is a person to be rescued who needs on-site CPR.

In some embodiments, the operator is the dispatcher of the emergency medical dispatching center, and the positive example is a patient who is encouraged by the dispatcher to start CPR by the help-seeker or other people present.

In some embodiments, the operator is the dispatcher of the emergency medical dispatching center, and the positive example is a person to be rescued of ROSC after on-site CPR.

In some embodiments, the system for helping the operator to question the help-seeker further includes a positive probability trend scatter plot acquisition module and a linear regression equation slope acquisition module.

The positive probability trend scatter plot acquisition module is configured to obtain a positive probability trend scatter plot according to a plurality of positive probabilities of the person to be rescued obtained in a plurality of rounds of dialogues between the operator and the help-seeker.

The linear regression equation slope acquisition module is configured to fit the positive probability trend scatter plot by using the linear regression equation and solve the linear regression equation to obtain the linear regression equation slope.

The positive probability trend scatter plot and the linear regression equation slope are used to represent the probability trend that the person to be rescued is a positive example. In the specific implementation process, the rounds of the dialogue corresponding to any positive probability amongst the plurality of positive probabilities can be taken as the abscissa and the any positive probability can be taken as the ordinate to obtain the coordinates on the positive probability trend scatter plot.

Figure 6A:
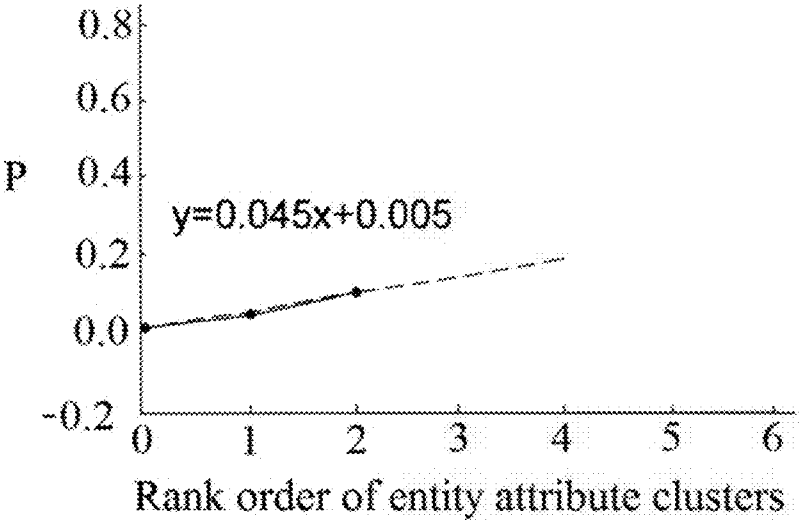
FIGS. 6A-6D are positive probability trend scatter plots obtained according to a plurality of chronological rounds of dialogues between different help-seekers and operators according to some embodiments of the present disclosure.
Figure 6B:
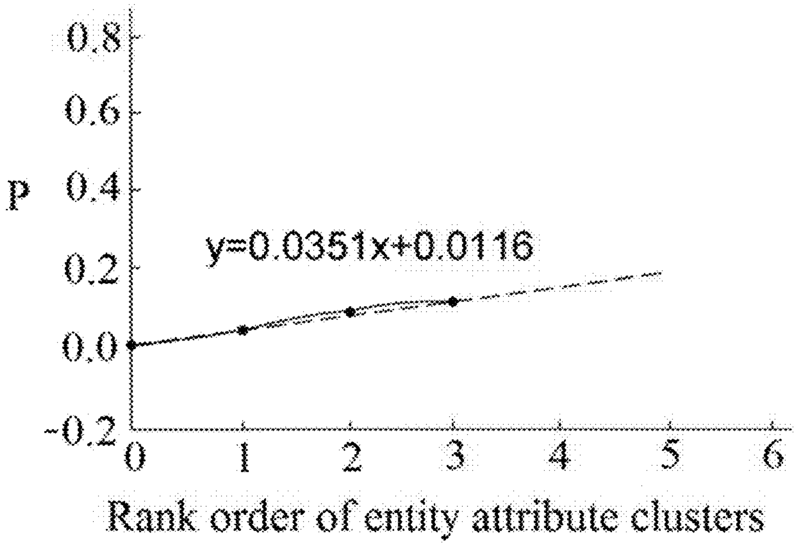
Figure 6B:
Figure 6C:
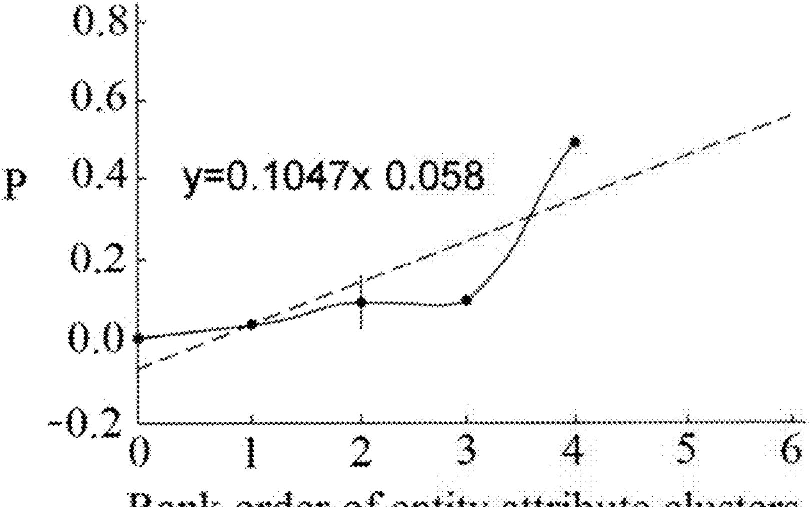
Figure 6D:
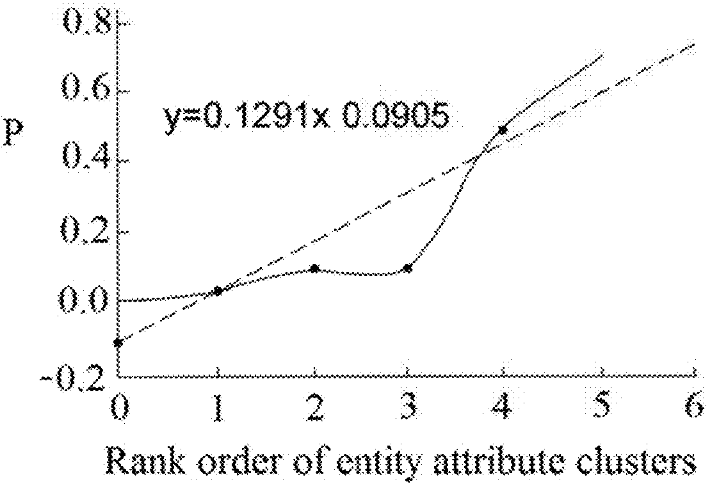

FIGS. 6A-6D are positive probability trend scatter plots obtained according to a plurality of chronological rounds of dialogues between different help-seekers and operators. The four slopes in FIGS. 6A-6D are 0.045, 0.0351, 0.1047 and 0.1291, respectively. Based on this, it is determined that the patient in FIG. 6D is most likely to have an outcome.

Figure 7A:
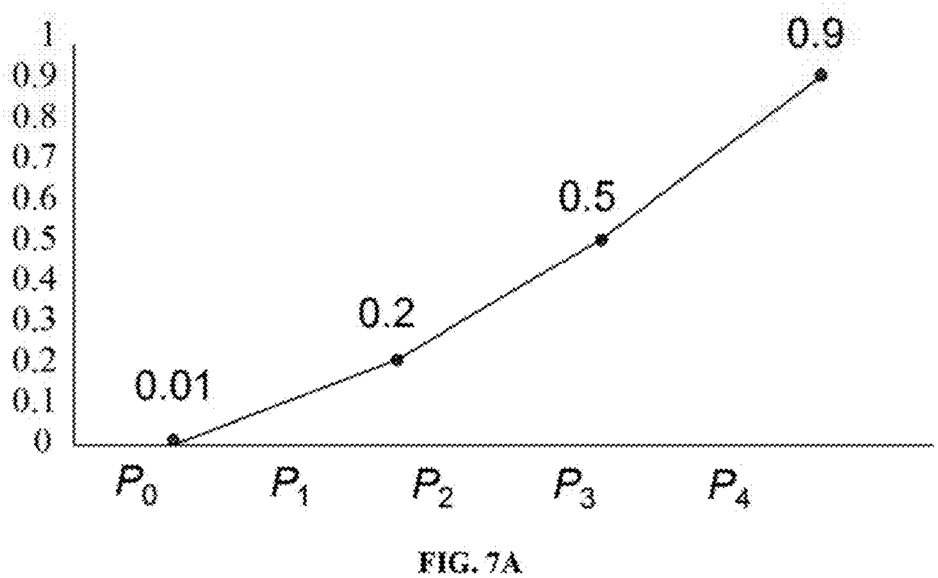
FIGS. 7A-7D are positive probability trend scatter plots obtained according to a plurality of chronological rounds of dialogues between different help-seekers and operators according to other some embodiments of the present disclosure.
Figure 7B:
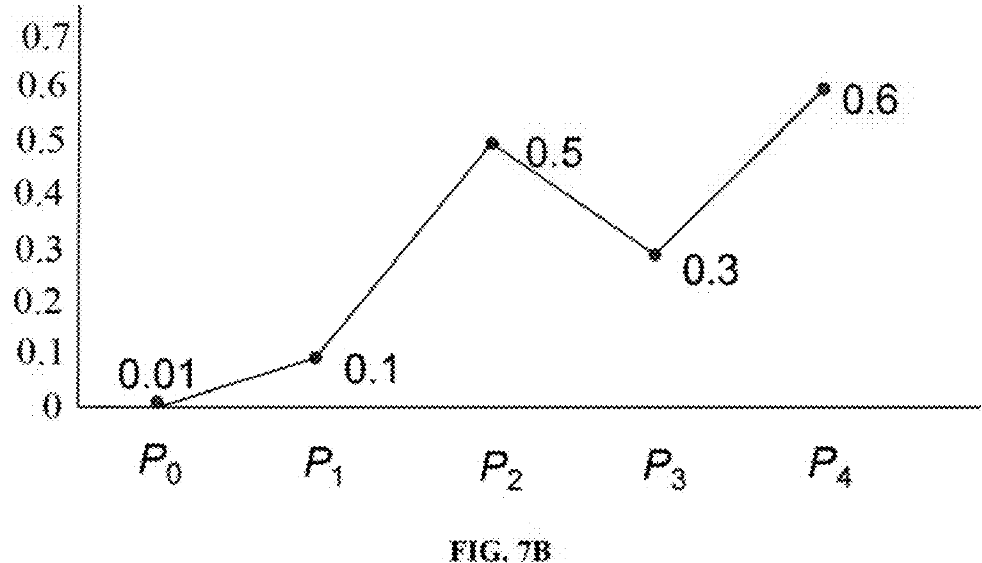
Figure 7C:
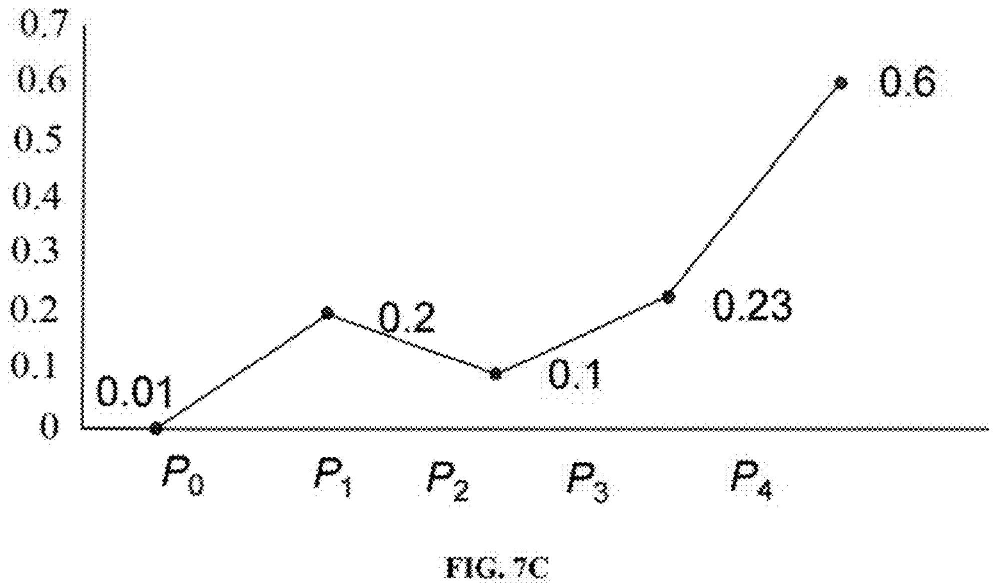
Figure 7D:
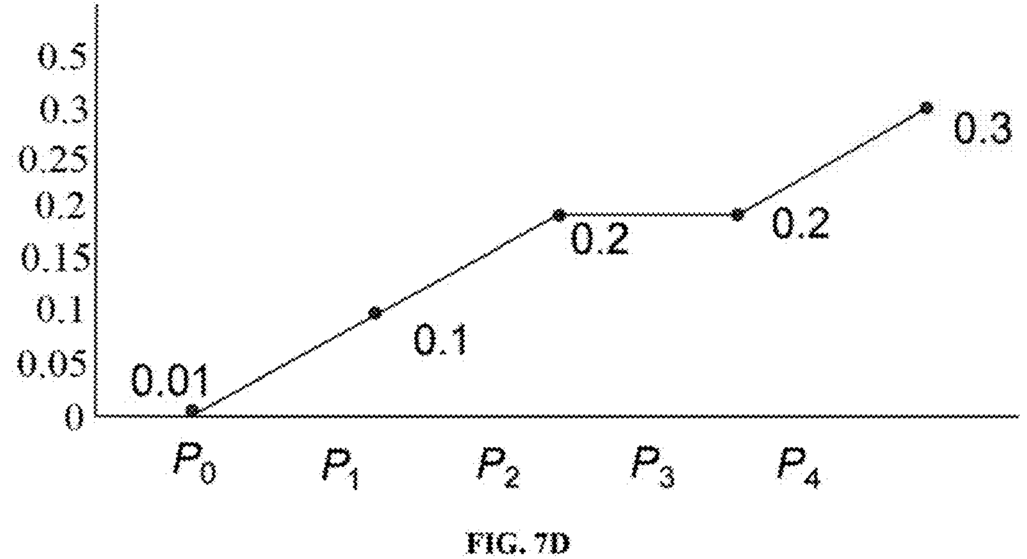

FIGS. 7A-7D are positive probability trend scatter plots obtained according to a plurality of chronological rounds of dialogues between different help-seekers and operators. In FIG. 7A, it indicates that the prediction probability of the outcome is quickly raised to 0.9 after only three iterations, and the possibility that the patient calling for help belongs to the true classification outcome is extremely high. In FIG. 7B, it indicates that the prediction probability of the outcome first rises, then falls and then rises, but the overall trend still tends to the true classification outcome. In FIG. 7C, it indicates that the previous iterations fail to "capture" the positive labels, but the last iteration quickly improves the prediction probability of the outcome. In FIG. 7D, it indicates that the probability of the true classification outcome is not high. The four slopes in FIGS. 7A-7D are 0.297, 0.138, 0.121 and 0.068, respectively. Based on this, it is determined that the patient in FIG. 7D is most likely to have an outcome.

In the positive probability trend scatter plot, because each person to be rescued is independent, and the questions and answers on each entity attribute cluster are independent, it is assumed that the variances of the random variable P (positive probability) under different x (abscissa) are equal to each other. According to Formula (2) and Formula (3), in combination with professional knowledge, y ($y=P$, $0 \leq P \leq 1$) generally increases with the increase of x. Therefore, the slope (b) of the linear regression equation ($y=a+bx$) can be used as the basis for determining the outcome, and the greater the b, the greater the positive probability of the person to be rescued in the future. In the specific implementation process, the least square method can be used to solve the linear regression equation to obtain the slope of the equation, and the calculation formula is as follows:

$$b = \frac{\sum_{i=0}^{p}(x_i - \overline{x})(y_i - \overline{y})}{\sum_{i=0}^{p}(x_i - \overline{x})^2} \quad \text{(Formula 5)}$$

In some embodiments, other regression models can also be used to fit the scatter plot, which is not limited by the description in this specification. For example, functions such as an inverse function, a power function, a logarithm function, a composite function, a growth function and an exponential function can be used to fit the scatter plot.

In some embodiments, the positive probability trend scatter plot and the linear regression equation slope can be shown (for example, displayed through the screen of the terminal 120) to the operator to help the operator to determine whether a person to be rescued is a positive example.

In some embodiments, the system for helping the operator to question the help-seeker further includes a rate ratio acquisition module and a rate difference acquisition module.

The rate ratio acquisition module is configured to obtain the rate ratio according to the ratio between the current positive probability of the person to be rescued and the positive probability of the person to be rescued obtained in the previous round of dialogue. The calculation formula of the rate ratio is as follows:

$$RR = \frac{P_c}{P_{c-1}} \quad \text{Formula (6)}$$

As an example only, if $P_1$ is 0.04 and $P_2$ is 0.1, the RR can be calculated as 2.5 according to Formula (6).

The rate ratio (RR) can indicate the value of the cut-off point selected in this round of dialogue to predict the true classification. When $RR>1$, the cut-off point selected in this round of dialogue has a discriminating value to the true classification. When $RR \leq 1$, the cut-off point selected in this round of dialogue has no distinguishing value to the true classification.

The rate difference acquisition module is configured to obtain the rate difference according to the difference between the current positive probability of the person to be rescued and the positive probability of the person to be rescued obtained in the previous round of dialogue. The calculation formula of the rate difference is as follows:

$$RD = P_c - P_{c-1} \quad \text{Formula (7)}$$

As an example only, if $P_1$ is 0.04 and $P_2$ is 0.1, the RD can be calculated as 0.06 according to Formula (7).

The rate difference (RD) can indicate the value of the cut-off point selected in this round of dialogue to predict the true classification. When $RD>0$, the cut-off point selected in this round of dialogue has a discriminating value to the true classification. When $RR \leq 0$, the cut-off point selected in this round of dialogue has no distinguishing value to the true classification.

In some embodiments, the rate difference and the rate ratio can be displayed to the operator to help the operator to determine the value of the positive probability of the current person to be rescued for determining whether the person to be rescued is a positive example.

When $RR>1$, the label has a distinguishing value to the true classification. When $RR \leq 1$, the label has no discriminating value to the true classification. When $RD>0$, the label has s distinguishing value to the true classification. When $RD \leq 0$, the label has no discriminating value to the true classification.

Another embodiment of the present disclosure provides a system for helping an investigator to question a respondent, wherein the system includes: a first reference group acquisition module, a classification test module, a receiver operating characteristic curve acquisition module, a candidate question semantic meaning acquisition module and a target question semantic meaning acquisition module.

The first reference group acquisition module is configured to select a plurality of first reference groups unprocessed from an initial reference group.

The first reference group is obtained by classifying a plurality of historical respondents amongst the initial reference group according to an entity attribute cluster. The entity attribute cluster consists of a plurality of entity attribute pairs corresponding to the same core question. The entity attribute pairs include entities and attributes. The entity represents the semantic meaning of a question from an investigator in a historical call for investigation, and the attribute represents the semantic meaning of an answer to the question from a respondent.

For details of the initial reference group, the first reference group, the entity attribute cluster and the entity attribute pair, refer to FIG. 2, which will not be described in detail here.

The classification test module is configured to take the positive probability of any second reference group included in any first reference group amongst the plurality of first reference groups as a cut-off point, and perform a classification test on any first reference group to obtain a classification sensitivity and a classification specificity corresponding to any second reference group.

The cut-off point is used to determine a positive label of the first reference group, and the second reference group is obtained by classifying the first reference group according to the entity attribute. For details of the second reference group and the cut-off point, refer to FIG. 2, which will not be described in detail here.

The receiver operating characteristic curve acquisition module is configured to obtain a receiver operating characteristic curve corresponding to any first reference group based on the classification sensitivities and the classification specificities corresponding to a plurality of second reference groups amongst any first reference group.

The candidate question semantic meaning acquisition module is configured to determine a target first reference group from the plurality of first reference groups according to the receiver operating characteristic curve corresponding to each first reference group amongst the plurality of first reference groups, and take the entity of each entity attribute pair in the entity attribute cluster corresponding to the target first reference group as a candidate question semantic meaning.

The target question semantic meaning acquisition module is configured to determine a target question semantic meaning from the candidate question semantic meaning according to the distance between a coordinate point corresponding to any second reference group amongst the plurality of second reference groups and a perfect classification coordinate point in the receiver operating characteristic curve corresponding to the target first reference group; wherein the perfect classification coordinate point is the coordinate point with the abscissa of 0 and the ordinate of 1 in the receiver operating characteristic curve, and the target question semantic meaning is used to help the investigator to conduct a next round of question.

In the above-mentioned embodiment of the system for helping the investigator to question the respondent, the specific processing of each module and its technical effects can refer to the relevant descriptions in the corresponding embodiment in FIG. 2, which will not be described in detail here.

Another embodiment of the present disclosure provides a system for helping an investigator to determine whether a respondent is a positive example, wherein the system includes: an entity attribute cluster and entity attribute pair determining module, a first reference group and second reference group determining module, a module for acquiring a number of members of predefined positive examples, and a positive probability determining module.

The entity attribute cluster and entity attribute pair determining module is configured to determine the entity attribute cluster currently corresponding to the respondent and the entity attribute pair currently corresponding to the respondent according to a question from the investigator and an answer to the question from the respondent in any round of dialogue between the investigator and the respondent.

The entity attribute cluster consists of a plurality of entity attribute pairs corresponding to the same core question, each entity attribute pair includes the entity and the attribute, the entity represents the semantic meaning of a question from the investigator in a historical call for investigation, and the attribute represents the semantic meaning of an answer to the question from the respondent.

For details of the entity attribute clusters and the entity attribute pairs, refer to the related contents in FIG. 2, which will not be described in detail here.

The first reference group and second reference group determining module is configured to acquire a first reference group corresponding to the entity attribute cluster and a second reference group corresponding to the entity attribute pair from an initial reference group.

The first reference group is obtained by classifying a plurality of historical respondents amongst the initial reference group according to an entity attribute cluster, and the second reference group is obtained by classifying the first reference group according to the entity attribute.

For details of the first reference group and the second reference group, refer to the related contents in FIG. 2, which will not be described in detail here.

The module for acquiring a number of members of predefined positive examples is configured to take the positive probability of the second reference group as a cut-off point to obtain the number of members of the first reference group who are predefined positive examples.

The cut-off point is used to determine the positive label of the first reference group. For details of the cut-off point, refer to the related contents in FIG. 2, which will not be described in detail here.

The positive probability determining module is configured to obtain the positive probability of the respondent according to the ratio between the number of members who are truly classified as positive examples amongst the members of the first reference group who are predefined positive examples and the number of members of the first reference group who are predefined positive examples.

The positive probability is used to help the investigator to determine whether a respondent is a positive example. For details of the positive probability and the positive example, refer to the related contents in FIG. 2, which will not be described in detail here.

The specific processing of each module in the above-mentioned embodiment of the system for helping the investigator to determine whether a respondent is a positive example and the technical effects can refer to the relevant descriptions in the corresponding embodiment in FIG. 3, which will not be described in detail here.

The above-mentioned system for helping the investigator to question the respondent and the system for helping the investigator to determine whether the respondent is a positive example can be applied to various application scenarios. For example, the systems can be applied to the epidemiological investigation of diseases or health conditions (abbreviated as epidemiological investigation) application scenarios, product after-sales service investigation application scenarios, etc. The epidemiological investigation task of infectious diseases is taken as an example for description hereinafter.

The epidemiological investigation is the key to controlling infectious diseases, and the information collected by the epidemiological investigation of infectious diseases can play a key role in effectively curbing infectious diseases. The purpose of epidemiological investigation of infectious diseases is to determine the action track of the respondent, people that the respondent met and events that the respondent happened in the past certain period of time, so as to provide a basis for clarifying the transmission chain, finding out the source of infection, determining close contacts, taking isolation measures and delineating the disinfection scope.

In some embodiments, the terminal used by the investigator can acquire the question from the investigator and the answer from the respondent, and send the question and the answer to the server for processing (or the terminal used by the investigator for processing). In some embodiments, the terminal used by the investigator can display the target question semantic meaning, the positive probability of the respondent, the rate ratio, the rate difference, and the positive probability trend scatter plot received from the server to the investigator in various ways (for example, voice prompt, text prompt, etc.), so as to help the investigator to determine the epidemiological investigation of the respondent (for example, whether the respondent is a close contact, whether the respondent is the person who needs to take isolation measures, etc.)

In the epidemiological investigation task scenario of infectious diseases, when the investigator tries to determine whether a respondent belongs to a certain group of people to whom specific measures need to be taken to prevent the spread of infectious diseases, the respondent who belongs to this group is a positive example, and the respondent who does not belong to this group is a negative example. For example, when the investigator (epidemiological investigator) determines whether the respondent is a close contact through dialogues, the positive example can be the respondent who belongs to a close contact, and the negative example can be the respondent who belongs to a non-close contact.

In the epidemiological investigation task scenario of infectious diseases, the predefined positive example is the group that the system assumes that the predefined positive example belongs to a certain group of people to whom specific measures need to be taken to prevent the spread of infectious diseases for the classification test or other calculation, and the predefined negative example is the group that the system (terminal or server used by the investigator) assumes that predefined negative example does not belong to a certain group of people to whom specific measures need to be taken to prevent the spread of infectious diseases for the classification test or other calculation. For example, when the investigator (epidemiological investigator) determines whether the respondent is a close contact through dialogues, the predefined positive example can be the respondent who belongs to the close contact assumed by the system, and the negative example can be the respondent who belongs to the non-close contact assumed by the system.

The basic concepts have been described hereinabove. Obviously, for those skilled in the art, the above detailed disclosure is only an example and does not constitute the limitation of the present disclosure. Although not explicitly described here, those skilled in the art may make various modifications, improvements and amendments to the present disclosure. Such modifications, improvements and amendments are suggested in the present disclosure, so that such modifications, improvements and amendments still belong to the spirit and scope of the exemplary embodiment of the present disclosure.

Meanwhile, the present disclosure uses specific words to describe the embodiments of the present disclosure. For example, "one embodiment", "an embodiment" and/or "some embodiments" mean a certain feature, structure or characteristic related to at least one embodiment of the present disclosure. Therefore, it should be emphasized and noted that "one embodiment" or "an embodiment" or "an alternative embodiment" mentioned twice or more times in different places in the present disclosure do not necessarily refer to the same embodiment. In addition, some features, structures or characteristics in one or more embodiments of the present disclosure can be appropriately combined.

In addition, unless explicitly stated in the claims, the order of processing elements and sequences, the use of numbers and letters, or the use of other names described in the present disclosure are not used to limit the order of the flow and the method of the present disclosure. Although some embodiments of the present disclosure that are presently considered useful have been discussed through various examples in the above disclosure, it should be understood that such details are only for illustrative purposes, and the appended claims are not limited to the disclosed embodiments. On the contrary, the claims are intended to cover all modifications and equivalent combinations that are in line with the spirit and scope of the embodiments of the present disclosure. For example, although the system components described above can be realized by hardware devices, the system components can also be realized only by software solutions, such as installing the described system on existing servers or mobile devices.

In the same way, it should be noted that in order to simplify the expression disclosed in the present disclosure and help to understand one or more embodiments of the present disclosure, in the previous description of the embodiments of the present disclosure, various features are sometimes merged into one embodiment, the attached drawings or the description thereof. However, such disclosure method does not mean that the object of the present disclosure needs more features than those mentioned in the claims. In fact, the features of the embodiment are less than all the features of the single embodiment disclosed above.

In some embodiments, numbers describing the number of ingredients and attributes are used. It should be understood that such numbers used in the description of embodiments are modified by the modifiers "about", "approximately" or "substantially" in some examples. Unless otherwise specified, "about", "approximately" or "substantially" means that the number allows a variation of plus or minus 20%. Accordingly, in some embodiments, the numerical parameters used in the specification and claims are approximate values, which can be changed according to the required characteristics of individual embodiments. In some embodiments, numerical parameters should consider the specified significant digits and use the method of reserving general digits. Although the numerical fields and parameters used to confirm the range and the breadth in some embodiments of the present disclosure are approximate values, in specific embodiments, such numerical values are set as accurately as possible within the feasible range.

For each of the patents, patent applications, patent application publications and other materials cited in the present disclosure, such as articles, books, specifications, publications, documents, etc., the entire contents are hereby incorporated into the present disclosure by

What is claimed is:

1. A system for helping an operator to question a help-seeker, comprising: a server and a terminal; wherein the terminal is configured to receive a current round of dialogue between the operator and the help-seeker, and send the current round of dialogue to the server; and the server is configured to:

receive the current round of dialogue from the terminal;

select an initial reference group based on the current round of dialogue, and select a plurality of first reference groups unprocessed from the initial reference group; wherein the first reference group is obtained by classifying a plurality of historical people to be rescued amongst the initial reference group according to an entity attribute cluster, the entity attribute cluster comprises a plurality of entity attribute pairs corresponding to a same core question, each entity attribute pair comprises an entity and an attribute, the entity represents a semantic meaning of a question from the operator in a historical call for help, and the attribute represents a semantic meaning of an answer to the question from the help-seeker;

set a positive probability of any second reference group comprised in any first reference group amongst the plurality of first reference groups as a cut-off point, and perform a classification test on any first reference group to obtain a classification sensitivity and a classification specificity corresponding to any second reference group; wherein the cut-off point is used to determine a positive label of the first reference group, and the second reference group is obtained by classifying the first reference group according to an entity attribute;

obtain a receiver operating characteristic curve corresponding to any first reference group based on classification sensitivities and classification specificities corresponding to a plurality of second reference groups amongst any first reference group;

determine a target first reference group from the plurality of first reference groups according to the receiver operating characteristic curve corresponding to each first reference group amongst the plurality of first reference groups, and set an entity of each entity attribute pair in an entity attribute cluster corresponding to the target first reference group as a candidate question semantic meaning; and determine a target question semantic meaning from the candidate question semantic meaning according to a distance between a coordinate point corresponding to any second reference group amongst the plurality of second reference groups and a perfect classification coordinate point in a receiver operating characteristic curve corresponding to the target first reference group; wherein the perfect classification coordinate point is a coordinate point with abscissa of 0 and ordinate of 1 in the receiver operating characteristic curve, and the target question semantic meaning is used to help the operator to conduct a next round of question;

wherein the terminal is further configured to receive the target question semantic meaning and present the target question semantic meaning in real time to the operator, and wherein the operator conducts the next round of question for the help-seeker based on the target question semantic meaning, to determine an on-site situation of a person to be rescued and a progress of the help-seeker in rescuing the person to be rescued.

2. The system according to claim 1, wherein setting the positive probability of any second reference group comprised in any first reference group amongst the plurality of first reference groups as the cut-off point, and performing the classification test on any first reference group to obtain the classification sensitivity and the classification specificity corresponding to any second reference group comprise:

setting members of the second reference group in the first reference group whose positive probability is greater than or equal to the cut-off point as predefined positive examples, and setting members of the second reference group in the first reference group whose positive probability is less than the cut-off point as predefined negative examples;

obtaining the classification sensitivity according to a number of members who are truly classified as positive examples in the predefined positive examples and a number of members who are truly classified as positive examples in the first reference group; and obtaining the classification specificity according to a number of members who are truly classified as negative examples in the predefined negative examples and a number of members who are truly classified as negative examples in the first reference group.

3. The system according to claim 2, wherein obtaining the receiver operating characteristic curve corresponding to any first reference group based on the classification sensitivities and the classification specificities corresponding to the plurality of second reference groups amongst any first reference group comprises:

setting the classification sensitivity of any second reference group amongst the plurality of second reference groups as the ordinate and an absolute value of a difference between the classification specificity of any second reference group and 1 as the abscissa, to obtain coordinate points corresponding to any second reference group; and connecting the coordinate points corresponding to each second reference group in the first reference group to obtain the receiver operating characteristic curve corresponding to any first reference group.

4. The system according to claim 1, wherein determining the target first reference group from the plurality of first reference groups according to the receiver operating characteristic curve corresponding to each first reference group amongst the plurality of first reference groups comprises:

calculating an area under curve of the receiver operating characteristic curve corresponding to each first reference group in the plurality of first reference groups; and setting the first reference group corresponding to a maximum area under curve as the target first reference group.

5. The system according to claim 1, wherein determining the target question semantic meaning from the candidate question semantic meaning according to the distance between the coordinate point corresponding to any second reference group amongst the plurality of second reference groups and the perfect classification coordinate point in the receiver operating characteristic curve corresponding to the target first reference group comprises:

calculating a plurality of distances between coordinate points corresponding to respective second reference groups in the plurality of second reference groups and the perfect classification coordinate point; and setting the second reference group corresponding to a shortest distance amongst the plurality of distances as a target second reference group, and setting an entity of entity attribute pair corresponding to the target second reference group as the target question semantic meaning.

6. The system according to claim 1, wherein the initial reference group is obtained by:

extracting personal characteristic information of the person to be rescued from a help-seeking sentence of the help-seeker, and determining the initial reference group according to the personal characteristic information.

7. A system for helping an operator to determine whether a person to be rescued is a positive example, comprising: a server and a terminal; wherein the terminal is configured to receive at least one round of dialogue between the operator and a help-seeker, and send the at least one round of dialogue to the server; and the server is configured to:

receive the at least one round of dialogue from the terminal;

determine an entity attribute cluster currently corresponding to the person to be rescued and an entity attribute pair currently corresponding to the person to be rescued according to a question from the operator and an answer to the question from the help-seeker in any round of dialogue between the operator and the help-seeker; wherein the entity attribute cluster comprises a plurality of entity attribute pairs corresponding to a same core question, each entity attribute pair comprise an entity and an attribute, the entity represents a semantic meaning of a question from the operator in a historical call for help, and the attribute represents a semantic meaning of an answer to the question from the help-seeker;

acquire a first reference group corresponding to the entity attribute cluster and a second reference group corresponding to the entity attribute pair from an initial reference group; wherein the first reference group is obtained by classifying a plurality of historical people to be rescued amongst the initial reference group according to the entity attribute cluster, and the second reference group is obtained by classifying the first reference group according to the entity attribute;

use a positive probability of the second reference group as a cut-off point to obtain a number of members of the first reference group who are predefined positive examples; wherein the cut-off point is configured to determine a positive label of the first reference group; and obtain the positive probability of the person to be rescued according to a ratio between a number of members who are truly classified as positive examples amongst the members of the first reference group who are predefined positive examples and the number of members of the first reference group who are predefined positive examples; wherein the positive probability is used to help the operator to determine whether the person to be rescued is the positive example;

wherein the terminal is further configured to receive the positive probability of the person to be rescued and present the positive probability in real time to the operator, and wherein the operator determines whether the person to be rescued is the positive example based on the positive probability, to determine an on-site situation of the person to be rescued and a progress of the help-seeker in rescuing the person to be rescued.

8. The system according to claim 7, wherein the server is further configured to:

obtain a positive probability trend scatter plot according to a plurality of positive probabilities of the person to be rescued obtained in a plurality of rounds of dialogues between the operator and the help-seeker; and fit the positive probability trend scatter plot by using a linear regression equation and solve the linear regression equation to obtain a linear regression equation slope;

wherein the positive probability trend scatter plot and the linear regression equation slope are used to represent a probability trend that the person to be rescued is the positive example.

9. The system according to claim 8, wherein obtaining the positive probability trend scatter plot according to the plurality of positive probabilities of the person to be rescued obtained in the plurality of rounds of dialogues between the operator and the help-seeker comprises:

setting the rounds of the dialogue corresponding to any positive probability amongst the plurality of positive probabilities as an abscissa and the any positive probability as an ordinate to obtain coordinates on the positive probability trend scatter plot.

10. The system according to claim 7, wherein determining the entity attribute cluster currently corresponding to the person to be rescued and the entity attribute pair currently corresponding to the person to be rescued comprises:

acquiring the question from the operator, and extracting question semantic meaning information from the question;

acquiring the answer to the question from the help-seeker, and extracting answer semantic meaning information from the answer;

determining a core question described in the question, and obtaining the entity attribute cluster according to the core question; and determining the entity attribute pair according to the question semantic meaning information and the answer semantic meaning information.

11. The system according to claim 7, wherein setting the positive probability of the second reference group as the cut-off point to obtain the number of members of the first reference group who are predefined positive examples comprises:

setting a number of members of the second reference group in the first reference group, whose positive probability is greater than or equal to the cut-off point as the number of members of the predefined positive examples.

12. The system according to claim 7, wherein the server is further configured to:

obtain a rate ratio according to a ratio between a current positive probability of the person to be rescued and a positive probability of the person to be rescued obtained in a previous round of dialogue; and obtain a rate difference according to a difference between the current positive probability of the person to be rescued and the positive probability of the person to be rescued obtained in the previous round of dialogue;

wherein the rate difference and the rate ratio are used to help the operator to determine value of the current positive probability of the person to be rescued in determining whether the person to be rescued is the positive example.

* * * * *